United States Patent
Wahlstrand et al.

(10) Patent No.: US 9,511,217 B2
(45) Date of Patent: Dec. 6, 2016

(54) ARCUATE INTRODUCER

(75) Inventors: Carl D. Wahlstrand, North Oaks, MN (US); John E. Kast, Hugo, MN (US); Gabriela C. Molnar, Fridley, MN (US); Glenna L. Case, Minneapolis, MN (US); Lisa M. Johanek, White Bear Lake, MN (US); Phillip C. Falkner, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 185 days.

(21) Appl. No.: 13/376,104

(22) PCT Filed: Jun. 21, 2010

(86) PCT No.: PCT/US2010/039300
§ 371 (c)(1),
(2), (4) Date: Dec. 2, 2011

(87) PCT Pub. No.: WO2010/148380
PCT Pub. Date: Dec. 23, 2010

(65) Prior Publication Data
US 2012/0078268 A1 Mar. 29, 2012

Related U.S. Application Data

(60) Provisional application No. 61/218,697, filed on Jun. 19, 2009.

(51) Int. Cl.
*A61B 19/00* (2006.01)
*A61N 1/05* (2006.01)
(Continued)

(52) U.S. Cl.
CPC .......... *A61N 1/0504* (2013.01); *A61B 17/3468* (2013.01); *A61M 25/0041* (2013.01); *A61M 25/01* (2013.01); *A61M 25/0105* (2013.01); *A61N 1/05* (2013.01)

(58) Field of Classification Search
CPC .......... A61B 19/201; A61B 2019/208; A61B 17/3468; A61N 2001/0578; A61N 1/056; A61N 1/0587; A61N 1/0504; A61N 1/05; A61M 25/01; A61M 25/0105; A61M 25/0041
USPC ............ 606/129; 607/116, 122, 124–126, 28
See application file for complete search history.

(56) References Cited

U.S. PATENT DOCUMENTS 4,512,351 A * 4/1985 Pohndorf ...................... 607/117
4,694,838 A * 9/1987 Wijayarthna et al. ........ 600/435
(Continued)

FOREIGN PATENT DOCUMENTS

WO   WO 2009131726 A1 * 10/2009 ............... A61N 1/05

OTHER PUBLICATIONS

PCT/US10/039299: Search Report and Written Opinion dated Sep. 6, 2010.
(Continued)

*Primary Examiner* — Amy R Weisberg
(74) *Attorney, Agent, or Firm* — Mueting, Raasch & Gebhardt, P.A.

(57) ABSTRACT

An introducer for a medical lead, the introducer having an arcuate component for creating an arcuate path in a patient. When used to percutaneously implant a medical device such as a medical lead with electrodes, the implanted lead has an arcuate configuration. The implanted lead can be used to at least partially encircle or bracket a region of chronic pain and provide therapeutic electrical signals to the region.

26 Claims, 9 Drawing Sheets

(51) Int. Cl.
*A61B 17/34* (2006.01)
*A61M 25/00* (2006.01)
*A61M 25/01* (2006.01)

(56) References Cited

U.S. PATENT DOCUMENTS

| | | | |
|---|---|---|---|
| 5,246,014 A * | 9/1993 | Williams et al. | 607/122 |
| 5,383,913 A | 1/1995 | Schiff et al. | |
| 5,690,611 A | 11/1997 | Swartz et al. | |
| 7,101,362 B2 * | 9/2006 | Vanney | 604/523 |
| 7,242,987 B2 | 7/2007 | Holleman et al. | |
| 7,349,742 B2 * | 3/2008 | Heil et al. | 607/116 |
| 7,515,964 B1 | 4/2009 | Alexander et al. | |
| 7,933,652 B2 | 4/2011 | Phillips et al. | |
| 8,244,378 B2 * | 8/2012 | Bly et al. | 607/127 |
| 8,280,528 B2 * | 10/2012 | Kuzma et al. | 607/137 |
| 8,311,647 B2 * | 11/2012 | Bly | 607/127 |
| 8,401,673 B2 * | 3/2013 | Bowe et al. | 607/122 |
| 2003/0144657 A1 * | 7/2003 | Bowe et al. | 606/41 |
| 2004/0102829 A1 * | 5/2004 | Bonner et al. | 607/125 |
| 2004/0102830 A1 * | 5/2004 | Williams | 607/125 |
| 2004/0147957 A1 * | 7/2004 | Pierson, III | 606/228 |
| 2005/0065588 A1 * | 3/2005 | Zhao et al. | 607/125 |
| 2006/0129203 A1 | 6/2006 | Garabedian et al. | 607/45 |
| 2006/0258978 A1 * | 11/2006 | Vanney | 604/95.01 |
| 2007/0239155 A1 | 10/2007 | Ibrahim et al. | |
| 2008/0058707 A1 * | 3/2008 | Ashley et al. | 604/21 |
| 2008/0058912 A1 * | 3/2008 | O'Brien | 607/116 |
| 2008/0269716 A1 | 10/2008 | Bonde et al. | |
| 2011/0160719 A1 * | 6/2011 | Govari et al. | 606/41 |
| 2012/0078268 A1 | 3/2012 | Wahlstrand et al. | |
| 2012/0083867 A1 | 4/2012 | Johnack et al. | |
| 2012/0290053 A1 * | 11/2012 | Zhang et al. | 607/116 |
| 2013/0006238 A1 * | 1/2013 | Ditter et al. | 606/41 |

OTHER PUBLICATIONS

PCT/US10/039300: Search Report and Written Opinion dated Oct. 26, 2010.

* cited by examiner

ARCUATE INTRODUCER

RELATED APPLICATION

This application is a U.S. National Stage filing under 35 U.S.C. 371 of copending PCT Application Ser. No. PCT/US2010/039300, filed Jun. 21, 2010, which claims the benefit of priority to U.S. provisional patent application no. 61/218,697, filed Jun. 19, 2009, both of which applications are incorporated herein by reference to the extent that they do not conflict with the present disclosure.

FIELD

This disclosure relates to implantable medical devices and methods for introducing medical leads into a patient.

BACKGROUND

Implantable electrical signal generators have been used successfully for treating a variety of diseases, including chronic pain. For example, chronic low back an leg pain have been successfully treated using implantable neurostimulator systems that apply electrical signals to selected regions of the spinal cord. While spinal cord stimulation can theoretically be used to treat many types of pain by altering afferent pain signals running through the spinal cord, some types of pain may be difficult to treat via spinal cord stimulation or may result in unintended side effects. In such situations, it may be desirable to apply pain treating electrical signals at peripheral areas closer in proximity to the pain.

Such peripheral nerve stimulation or peripheral nerve field stimulation, as it is often called, does not have as long of a history of use for treatment of pain with implantable medical devices, relative to spinal cord stimulation. Accordingly, new methods, techniques and devices for application of electrical signals to the periphery for treating pain are still being developed. For example, new methods, techniques and devices may be needed to ensure that leads for applying electrical signals to peripheral nerves are properly positioned when implanted so that electrical signals emitted from the lead "capture" the desired peripheral nerves.

BRIEF SUMMARY

The present disclosure describes, among other things, an introducer for a medical lead. The introducer has an arcuate component for creating a curved path through tissue of a patient. The arcuate component of the introducer may have lumen for passage of the lead therethrough. Thus, after insertion of the lead in the lumen and withdrawal of the introducer, the lead may be positioned along the curved path of the patient created by the introducer. Alternatively, the lead may be attached to a distal portion of the introducer. As the introducer is withdrawn from the patient, the lead may be pulled along the curved path created by the introducer, properly positioning the lead in the patient. Regardless of the embodiment of the introducer or method employed, the lead may be positioned along the curved path created by the introducer and thus may assume a curved implanted shape. The implanted lead, depending on the shape and interstitial path of the introducer, can be used to at least partially encircle or bracket a region of interest, such as a region of chronic pain, and to provide electrical stimulation to the region.

Such introducers and implantation methods may be particularly well suited for treatment of pain where nerve trunks associated with the pain are superficial in the region of the pain, such as with pain associated with herniorraphy. In such cases, the lead may be positioned to encircle or bracket the nerve trunks. In any case, electrical signals emitted from leads positioned to encircle or bracket a region of pain may produce sufficient paresthesia for pain relief.

In various embodiments, an introducer includes a shaft; a radial component; and an arcuate component having a proximal end and a distal end. The arcuate component is connected the radial component, and the radial component is connected to the shaft. The arcuate component extends along a closed path (e.g., a circular or elliptical path) at least 90 degrees (e.g., at least 180 degrees, or at least 270 degrees). A lumen for receiving a lead may extend through the arcuate component, the radial component, and at least a portion of the shaft.

In various embodiments, an introducer includes a shaft, a radial component, and an arcuate component having a proximal end and a distal end. The arcuate component is connected to the radial component, and the radial component is connected to the shaft. A lumen for receiving a lead passes through the entire arcuate component, the entire radial component and through the shaft to an inlet on the shaft. In some embodiments, the introducer includes a depth control element, such as a plate. The arcuate component may extend 90 degrees, 180 degrees, 270 degrees, up to 360 degrees, and any angle therein. The arcuate component may be semi-circular, having a constant radius from the shaft. The shaft may be perpendicular to the arcuate component. The introducer may have an optional handle to facilitate use.

In some embodiments, a method of implanting a lead to at least partially encircle a site includes implanting a lead in proximity to the site by passing the lead through a lumen of an arcuate component of an introducer. The arcuate component is percutaneously positioned. The implanting process may include rotating the arcuate component around an axis.

In some embodiments, a method of implanting a lead to at least partially encircle a site includes coupling a distal end portion of a lead to a distal end of an the arcuate component of an introducer. The arcuate component of the introducer may then be withdrawn from a patient along a curved path at least partially encircling the site.

These and various other features and advantages will be apparent from a reading of the following detailed description.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the apparatuses, systems and methods described herein. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "representative" and "exemplary" are used in the context of "providing an example" and do not necessarily indicate that the example provided is superior to, or more particularly suited for the intended purpose than, other potential examples.

The present disclosure describes, among other things, a medical lead introducer having curved member for creating a curved path within tissue of a patient. The curved member may have a lumen for passing a medical lead therethrough for percutaneous implantation. In some embodiments, a lead may be attached to a distal end portion of the introducer. The lead may then be pulled through the curved path created by the introducer as the introducer is withdrawn from the patient. In many embodiments, the implanted lead can be positioned such that electrodes of the lead at least partially encircle or bracket a region of chronic pain. Application of electrical signals via electrodes may then effectively capture the appropriate nerve and be configured to alleviate the pain.

Figure 1:
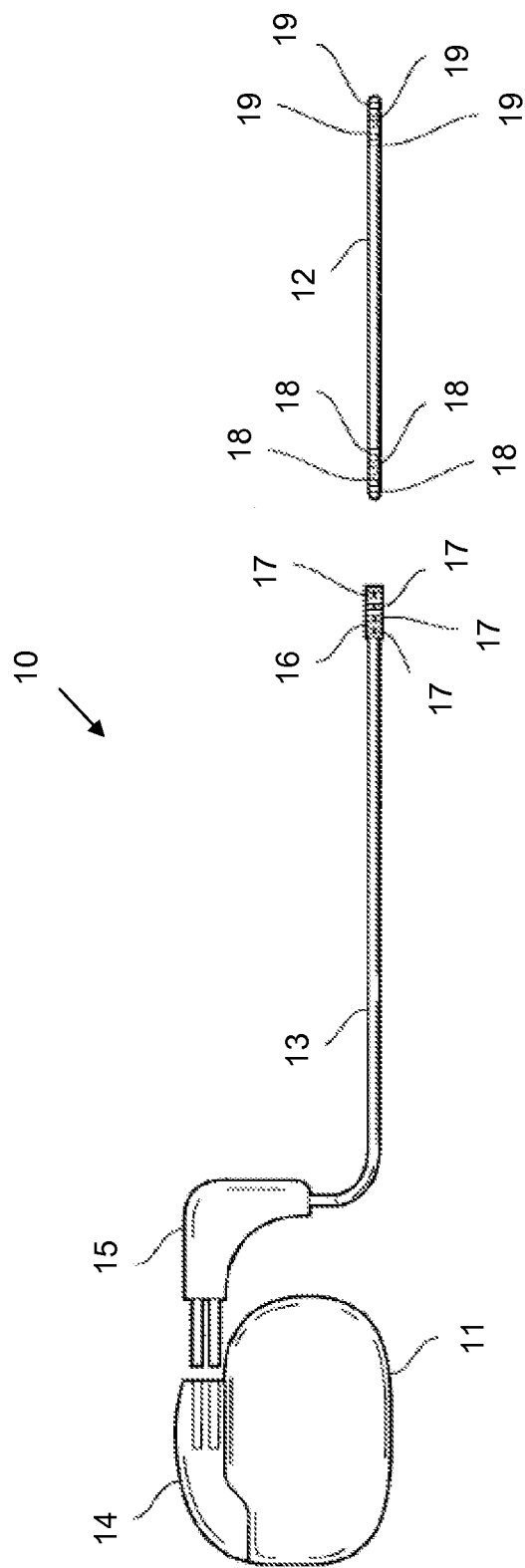
FIG. 1 is a schematic side view of a generic implantable electrical system.

Any suitable electrical signal generator system may be employed for applying electrical signals in such a manner. For example and referring to FIG. 1, a side view of an embodiment of a representative system 10 is shown. System 10 includes an implantable electrical signal generator 11, a lead extension 13 and a lead 12. Implantable electrical signal generator 11 includes a connector header 14 configured to receive plug 15 at proximal end of lead extension 13 or other adaptor to operably couple lead 12 to electrical signal generator 11. The distal end portion of lead extension 13 includes a connector 16 configured to receive proximal end portion of lead 12. Connector 16 includes electrical contacts 17 configured to electrically couple extension 13 to lead 12 via electrical contacts 18 on the proximal end portion of lead 12. Electrodes 19 are present on distal end portion of lead 12 and are electrically coupled to electrical contacts 18 through conductors (not shown) within lead 12. In general, lead 12 may include any number of electrodes 19, e.g. one, two, three, four, five, six, seven, eight, sixteen or any other number. In some embodiments, each electrode 19 is electrically coupled to a discrete electrical contact 18, whereas in other embodiments, a set of electrodes 19 is electrically coupled to a discrete contact 18. While not shown, it will be understood that more than one lead 12 may be operably coupled to one electrical signal generator 11 or one extension 13 or that more than one extension 13 may be operably coupled to one electrical signal generator 11. It will be further understood that lead 12 may be coupled to electrical signal generator 11 without use of extension 13 or other adaptor.

In order to position a lead in a patient in a manner than allows the electrical signals applied by the electrodes to affect targeted tissue of the patient (e.g., an afferent nerve fiber), an introducer may be employed to tunnel a path through tissue of the patient in proximity to the region to be treated (e.g., a region of chronic pain). The lead may be inserted into a lumen of the introducer. Then, by withdrawing the introducer over the lead and from the patient, the lead is left implanted in the patient along the path created by the introducer. Alternatively, a lead may be attached to a distal portion of the introducer, and as the introducer is withdrawn from the patient, the lead is pulled through the path created by the introducer.

The present disclosure is directed to an introducer having an arcuate component that results in an implanted lead having a curved path.

Figure 2:
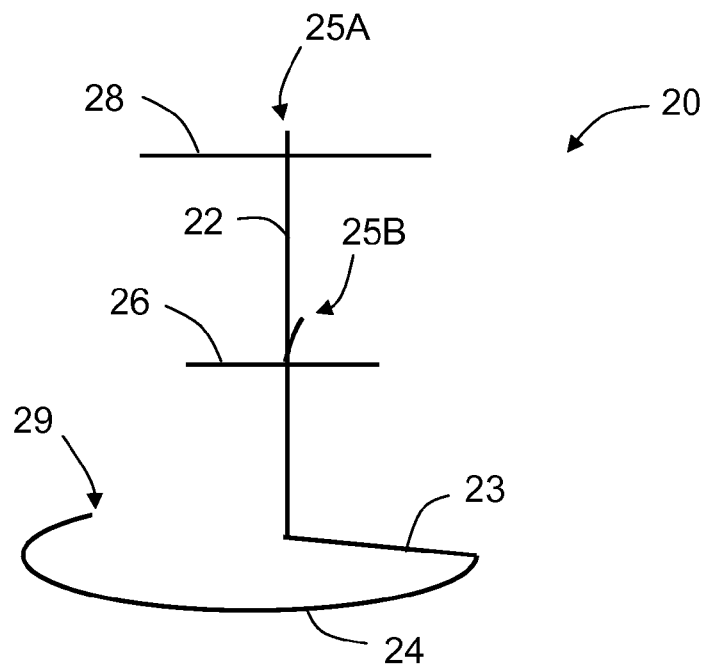
FIGS. 2-4 are a schematic perspective views of embodiments of arcuate introducers.
Figure 3:
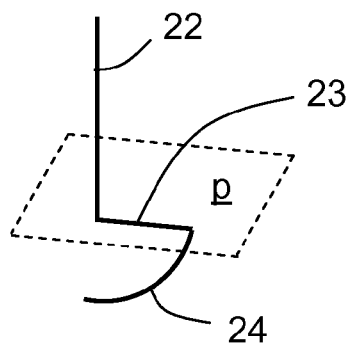
Figure 4:
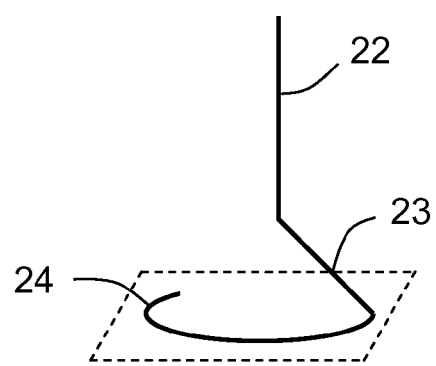
Figure 5A:
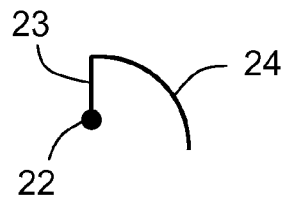
FIGS. 5A-5F are schematic top views of embodiments of arcuate introducers.
Figure 5B:
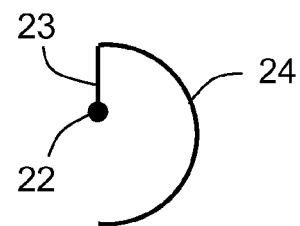
Figure 5C:
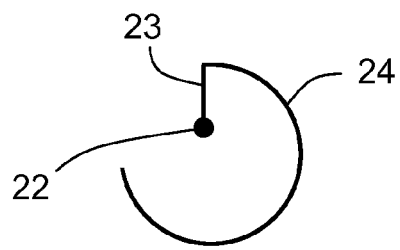
Figure 5D:
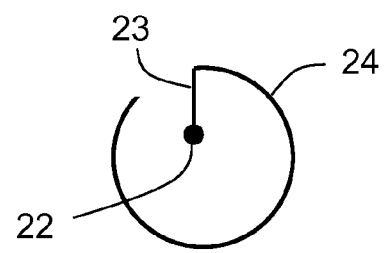
Figure 5E:
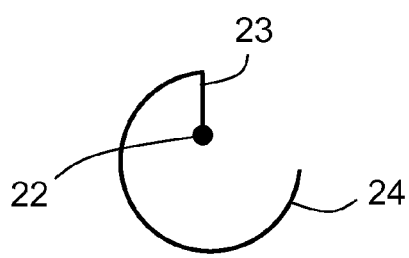
Figure 5F:
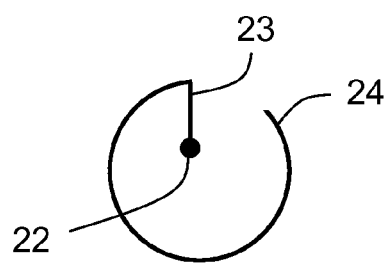

FIGS. 2-4 illustrate various embodiments of introducers 20. In the depicted embodiments, introducer 20 has a shaft 22 connected to a radial component 23 and an arcuate component 24. The distal most end 29 of arcuate component 24 may be blunt or have a sharp end to facilitate advancement of arcuate component 24 through tissue of a patient.

Arcuate component 24 may be substantially planar (see, e.g., FIG. 2 and FIG. 4) or may be non-planar (see, e.g., FIG. 3), in which the arcuate component 24 extends below a plane (p) in the direction of the shaft 22 (from proximal to distal). Arcutate component 24 may extend to any extent along a curved path. For example, when the arcuate component 24 is nonplanar along its length, the arcuate component may be helical (or semi-helical), corkscrew-shaped (or semi-corkscrew shaped), or the like. By way of further example, when the arcuate component 24 is planar or substantially planar, the arcuate component may be circular or semi-circular, elliptical or semi-elliptical, oval or semi-oval, wishbone-shaped or semi-wishbone shaped, or the like.

Arcuate component 24 may extend any amount along the curved path. For example, arcuate component 24 may extend 90 degrees or more, 135 degrees or more, 180 degrees or more 225 degrees or more, 270 degrees or more 315 degrees or more, about 360 degrees, or even more than 360 degrees along a curved path. As used herein, an arcuate component 24 that "extends a specified number of degrees" extends along a curved path to the extent that the arcuate component would extend along a circular path. For example, an arcuate component that extends 180 degrees along an elliptical path extends half way around the elliptical path. Arcuate component 24 may extend clockwise or counterclockwise along a curved path.

In many embodiments, the arcuate component 24 extends, at least partially, over a closed path. A closed path is a path that has the same beginning and end point, such as a circle, an oval, an ellipse, or the like. For the purposes of the present disclosure, a non-planar arcuate component may be considered to extend along a closed path if its projected shape has a closed path along a plane. That is, if the rectilinear projection of the arcuate component onto a plane normal to the unit vector (often in the direction of the shaft) is along a closed path, then the arcuate component is considered to extend along a closed path. By way of example, if the arcuate component is helical or semi-helical, the projected shape of the helix or semi-helix may be circular or semi-circular. Thus, the helical or semi-helical arcuate component will be considered to extend along a closed path for purposes of the present disclosure.

When arcuate component 24 is semi-circular, the arcuate component has a constant radius from shaft 22 along the length of arcuate component 24; in some embodiments, this radius is the length of radial component 23. In some embodiments, however, arcuate component 24 may be oval, elliptical or otherwise arcuate with a non-constant radius from shaft 22.

In the embodiments depicted in FIGS. 2-4, the radial component 23 connects the shaft 22 to the arcuate component 24 such that twisting the shaft 22 results in rotation of the arcuate component 24. As shown in FIG. 2, the introducer 20 may have a handle 28, which can facilitate holding the introducer 20 in the desired position during implantation of a lead. The handle 28 may alternately provide torsional leverage to the physician during use of introducer 20. For example, the handle 28 may facilitate twisting of the shaft 22, and thus facilitate rotation of the arcuate component 24 as it is being advanced through tissue of a patient. The handle 28 may be permanently affixed to, or form a part of, the shaft 22 or may be removable from the shaft. Any suitable handle configuration other than, or in addition to, the T-shaped handle depicted in FIG. 2 may be employed.

The shaft 22, radial component 23 and arcuate component 24 may each be separately formed and joined or connected or may be formed as a single unit, or a combination thereof. The radial component 23 may be coplanar with the arcuate component (see, e.g., FIG. 2 and FIG. 3).

In some embodiments, e.g. as depicted in FIG. 2 and FIG. 4, the radial component 23 is perpendicular to the shaft 22. That is, shaft 22 and arcuate component 24 are positioned at an angle of 90 degrees to each other.

In some embodiments, e.g. see FIG. 4, the radial portion 23 extends from the handle at an angle greater than 90 degrees. Of course, the radial component 23 may extend from the shaft 22 at any suitable angle. Radial component 23, in some embodiments, may be coplanar with arcuate component 24, and thus, the distal end of shaft 22 will also be coplanar with arcuate component 24. When the arcuate component 24 is planar, the axis of the shaft 22 may be normal to the plane or may extend at any other angle from the plane. Preferably, the shaft 22 is positioned such that twisting the shaft results in turning of the arcuate component 24 in a manner that allows the arcuate component 24 to tunnel through tissue of a patient.

Referring back to FIG. 2, the introducer 20 may include a depth control member 26, spaced from arcuate component 24 along the shaft 22, to limit the depth to which arcuate component 24 can be implanted. That is, the depth control member 26 engages a patient's skin in use such that the depth at which arcuate component 29 may tunnel within the patient is limited. Any suitable depth control member 26 may be employed, such as a bar, plate, or the like. The depth control member 26 may be permanently affixed to the shaft 22 or may be moveable and re-lockable relative to shaft 22 so that the depth at which arcuate component 24 may be implanted can be varied. The depth control member 26 will typically be parallel to the plane of arcuate component 24. As indicated above, arcuate component 24 is preferably planar, with the distal end and the proximal end of arcuate component 24 defining a plane that is parallel to depth controller 26. More preferably, the entire length of arcuate component 24 is planar and parallel to depth consistency plate 26 to maximize the control of the depth at which the arcuate component 24 may be implanted. In some embodiments, e.g. when used to implant implanting a lead in proximity to a peripheral nerve, the desired depth of arcuate component 24 is under the subcutaneous layer, between the subcutaneous layer and any fatty layer.

As described above and with reference to FIG. 2, introducer 20 may have a lumen through which a lead may be introduced. The arcuate component 24 of the introducer 20 may be withdrawn from a patient and over lead, which is positioned in the lumen, leaving the lead positioned in path tunneled by the arcuate component 24 of the introducer 20, as will be described in more detail below. In the embodiment depicted in FIG. 2, at least a portion of the shaft 22 has a lumen therein. Both the radial component 23 and the arcuate component 24 have lumens therethrough. The lumens of the shaft 22, radial component 23 and arcuate component 24 are in communication with each other and allow passage of a lead through the respective lumens. The depicted introducer 20 includes an inlet port for receiving a lead into the lumen of shaft 22, radial component 23 and curved component 24. One suitable location for an inlet port 25A is illustrated at the proximal end of shaft 22. In this embodiment, the entire length of shaft 22 from inlet port 25A to radial component 23 would have the lumen therethrough. Another suitable location for an inlet port 25B is illustrated between the proximal end of shaft 22 and the distal end of shaft 22 (where radial component 23 begins). In such embodiments, only the length of shaft 22 between inlet port 25B and radial component 23 would need the lumen therethrough. In the embodiment depicted in FIG. 2, the depth control member 26 is positioned between arcuate component 24 and inlet port 25A, 25B.

Of course and as discussed above, in embodiments where the lead is pulled through tissue of the patient by the introducer 20, the introducer 20 might not have a lumen. Introducers and methods for implanting a lead with such introducers will be described in more detail below.

Referring now to FIGS. 5A-F, six possible configurations of an introducer are shown in top views, where the arcuate component 24 is semi-circular. In the depicted embodiment, the shaft 22 is positioned in the center of the circle of the semicircle of the arcuate component 24. In the depicted embodiment, twisting the shaft 22 about its axis will cause the arcuate component 24 to follow a circular path. Thus, the depicted introducers can be used to tunnel semi-circular paths within a patient. The arcuate components in FIGS. 5A-F extend about 90 degrees (5A), about 180 degrees (5B), about 270 degrees (5C, 5E) or about 310 degrees (5D, 5F). Of course, the arcuate component 24 may extend any suitable number of degrees, such as more than 270 degrees, but less than 360 degrees. The arcuate components 24 in FIGS. 5A-D extend from the radial component 23 in a clock-wise manner, where the arcuate components 24 in FIGS. 5E-F extend from the radial component 23 in a counter clock-wise manner.

Figure 6:
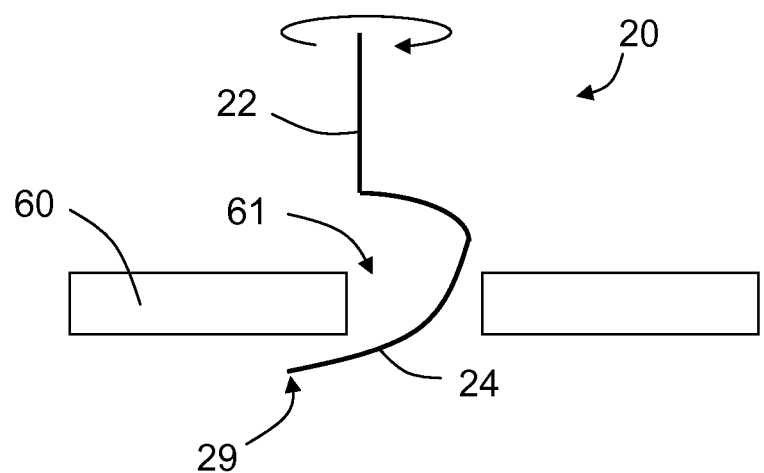
FIG. 6 is a schematic side view of an arcuate introducer partially implanted in a patient.

Referring now to FIG. 6, a schematic view of an introducer 20 being inserted into a patient through an incision 61 in the skin 60 of the patient. The distal end 29 of the arcuate component 24 is first inserted through the skin 61, in this case through the incision 61. However, it will be understood that an incision need not be made in all cases, particularly wherein distal end 29 is sharp and capable of piercing the skin 60. Once the distal end 29 of the arcuate component 24 is through or past the skin 60, the shaft 22 may be twisted about its axis if arcuate component is semi-circular (or otherwise if arcuate component is not semicircular) to cause arcuate component 24 to tunnel a semi-circular path beneath the skin 60 of the patient. If the introducer includes a depth control member (not shown in FIG. 6, but see, e.g., element 26 of FIG. 2), the introducer may be inserted in the patient to a depth until control member retards further insertion.

Figure 7:
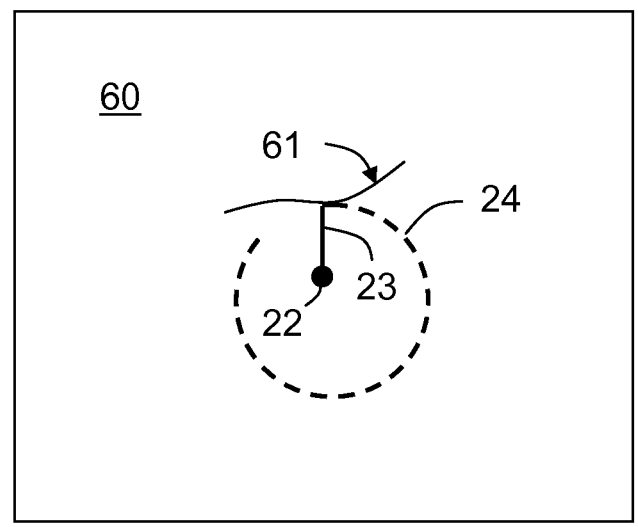
FIG. 7 is a schematic top view of an arcuate introducer implanted in a patient with the dashed lines indicating portions beneath the skin of a patient.

A top view of an introducer 20 according to FIG. 6 implanted in the patient is shown in FIG. 7. As shown, the shaft 22 is offset from the incision 61 (or point of entry) in the skin 60 by a distance equal to the radial distance that the radial component 23 extends from the shaft 22. The dashed line refers to the arcuate component 24 beneath the skin 60 of the patient.

Figure 8A:
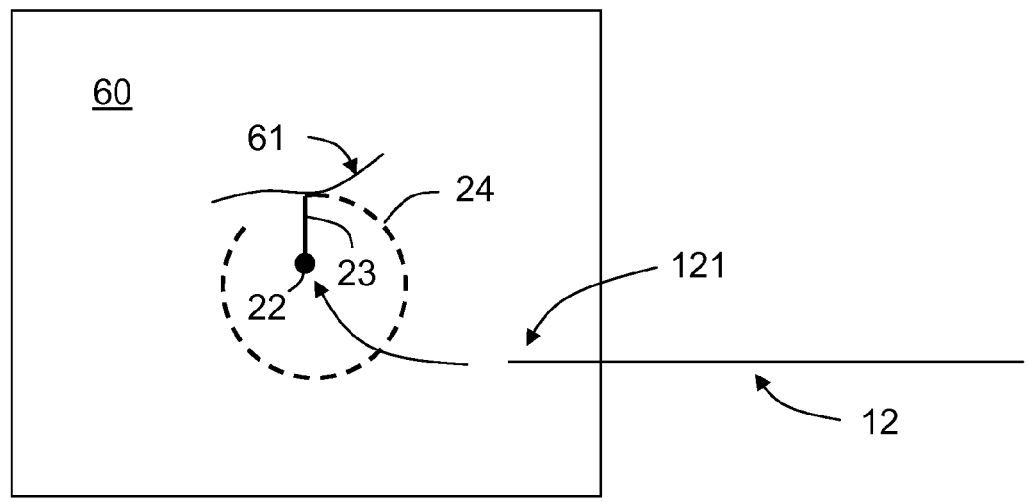
FIGS. 8A-C are schematic top views illustrating a process of using an arcuate introducer to implant a lead in a patient.
Figure 8B:
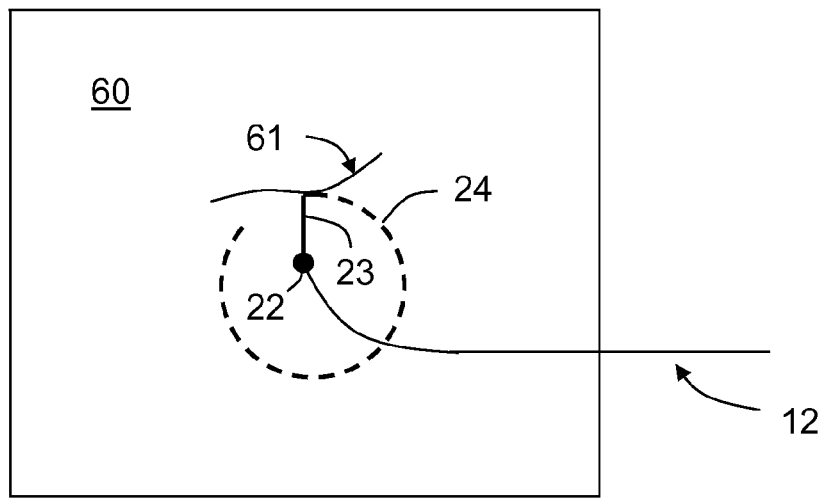
Figure 8C:
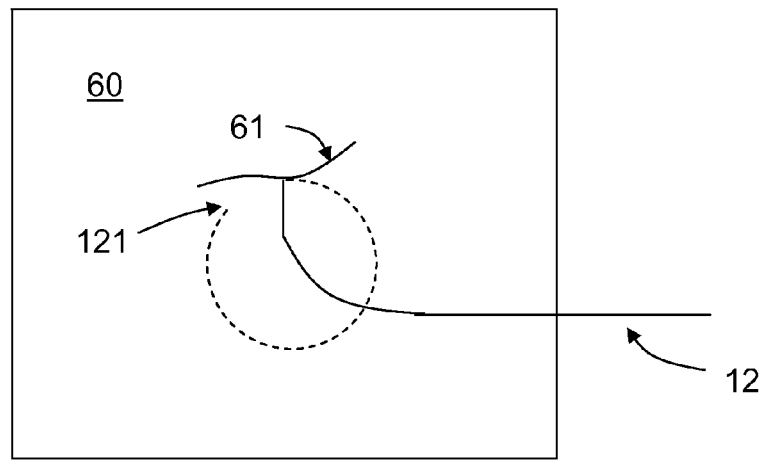

Referring now to FIGS. 8A-C, an embodiment where the introducer has a lumen through which a lead 12 may be inserted is shown. That is, at least a portion of the shaft 22, the length of the radial component 23 and the length of the arcuate component 24 has a lumen extending therethrough. The distal end 121 of the lead 12 is inserted into the lumen (e.g., via inlet 25A, 25B as shown in FIG. 2). The lead 12 is then fed through the shaft 22, radial component 23 and into arcuate component 24 of the introducer 20 that is properly positioned under the skin 60. Of course, the lead may be fed into the introducer before piercing the patient's skin 60 with the distal end of the arcuate component 24 (or insertion through incision 61) or at any time during the proper positioning of the introducer, or portion thereof, under the patient's skin. In any case, the lead 12 may be inserted until resistance is met and impedes further lead advancement (e.g., when distal end of arcuate component 24 is at lead partially inserted into patient) or until the distal end 121 of the lead 12 extends beyond the distal end of arcuate component 24 (e.g., before the introducer is implanted in the patient). Once the introducer is fully implanted and the lead 12 is inserted into the introducer, the introducer may be removed, e.g. by counter clockwise rotation of shaft 23 about its central axis in the embodiment depicted in FIG. 8B. As the introducer is removed, in some embodiments, simultaneous feeding of the lead 12 through the lumen of the introducer results in the lead 12 maintaining the appropriate implanted position in the patient. Thus, the lead 12 is left properly positioned along the curved path under the skin of the patient, which the distal end 121 of the lead 12 being substantially in the same position that was previously occupied by the distal end of the arcuate component 24 of the introducer (see, FIG. 8C). The proximal end of the lead 12 may then be tunneled subcutaneously to an appropriate location of the patient, e.g. to a location of an implanted electrical signal generator using standard introducers as well known in the art.

Figure 9A:
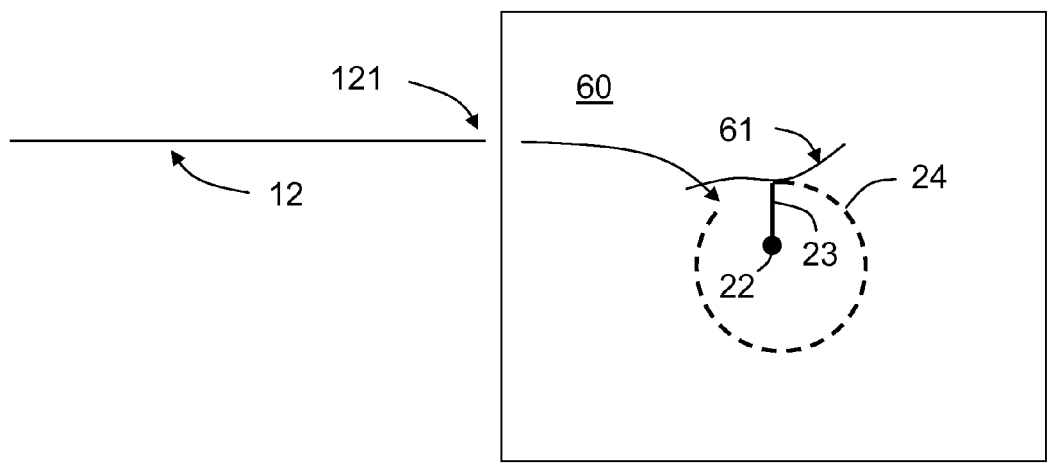
FIGS. 9A-B are schematic top views illustrating a process of using an arcuate introducer to implant a lead in a patient.
Figure 9B:
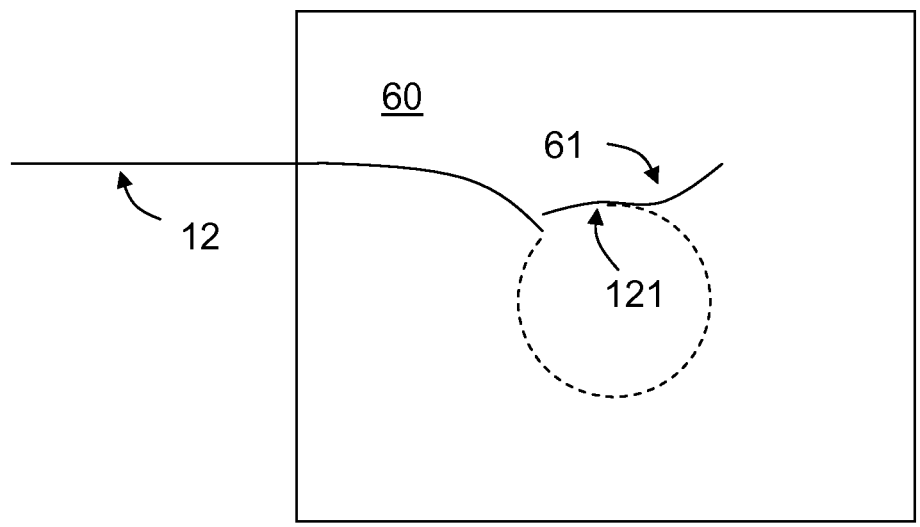

Referring now to FIGS. 9A-B, an embodiment where the distal end 121 of the lead 12 is attached to the distal end of the arcuate component 24 after the arcuate component 24 of the introducer is properly positioned under the skin 60 of the patient is shown. A second incision (not shown) may be made to allow the distal end 121 of the lead 12 access to the distal end of the arcuate member 24. Alternatively, when the arcuate member 24 extends about 360 degrees the implanted subcutaneous end of the arcuate member 24 may be accesses through the first incision 61, if present. The distal end 121 of the lead 12 may be attached to the distal end of the arcuate component 24 of the introducer via any suitable mechanism. For example, the distal end 121 of the lead 12 and the distal end of the arcuate component 24 may both include a loop (not shown) through which a suture may be placed so that the distal end of the lead and the distal end of the arcuate member may be coupled via a suture wire or thread. Alternatively or in addition, the lead 12 or arcuate component 24 may include a suture bump, recess or the like. The distal end 121 of the lead 12 or the distal end of the arcuate component 24 may include a capture mechanism (e.g., clamp, set screw, Luer lock, or the like—not shown) to engage and capture the lead 12 to the arcuate component 24. Once the distal end 121 of the lead 12 is attached to the distal end of the arcuate component 24, the introducer may be withdrawn from the patient; e.g. by counterclockwise rotation of the shaft 23 about its central axis in the depicted embodiment in FIGS. 9A-9B. The distal end of the lead 12 may be detached from the distal end of the arcuate component 24, e.g. either subcutaneously at incision 61 site or external to the patient. The lead 12 will then be left implanted along the path created by the arcuate component 24 of the introducer under the skin 60 of the patient (see, e.g. FIG. 9B).

Figure 10:
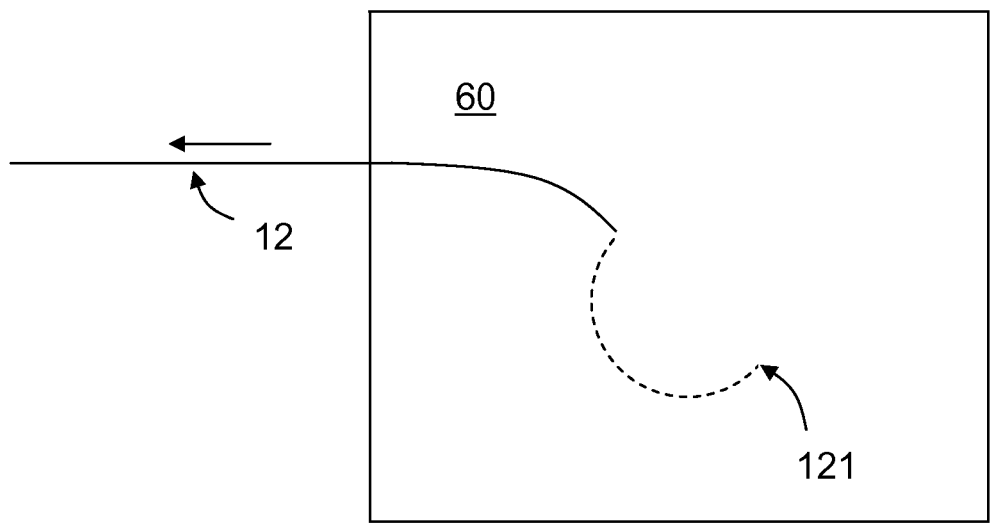
FIG. 10 is a schematic top view of a portion of a lead implanted under the skin of a patient, with dashed lines indicating the portion beneath the skin.

Whether implanted through a lumen of an introducer or by pulling by attachment to a distal end of an introducer, a lead may, if necessary or desired, be pulled proximally to withdraw the distal end of the lead along the path created by the introducer. For example and with reference to FIG. 10, the distal end 121 of the lead 12 is withdrawn within the subcuataneous path created by the introducer so that the lead extends along the path to an extent less than the arcuate component of the introducer (compare to FIG. 8C or FIG. 9B, e.g., 180 degrees compared to about 360 degrees).

In some embodiments where the implanted lead follows an arcuate path of about 360 degrees, the distal end of the lead may be secured to a more proximal part of the lead at the beginning point of the arcuate path. For example, the distal end of the lead may include a feature (e.g., loop, bump, recess, etc.) to facilitate suturing the more proximal part of the lead to the distal end. The more proximal part may also include a feature or be reinforced to accept the suture. Alternatively or in addition, the distal end of the lead or the more proximal portion of the lead may include a capture feature (e.g. as discussed above in the text associated with FIG. 9). Forming a secured loop in the implanted lead may reduce lead migration following implantation.

Figure 11:
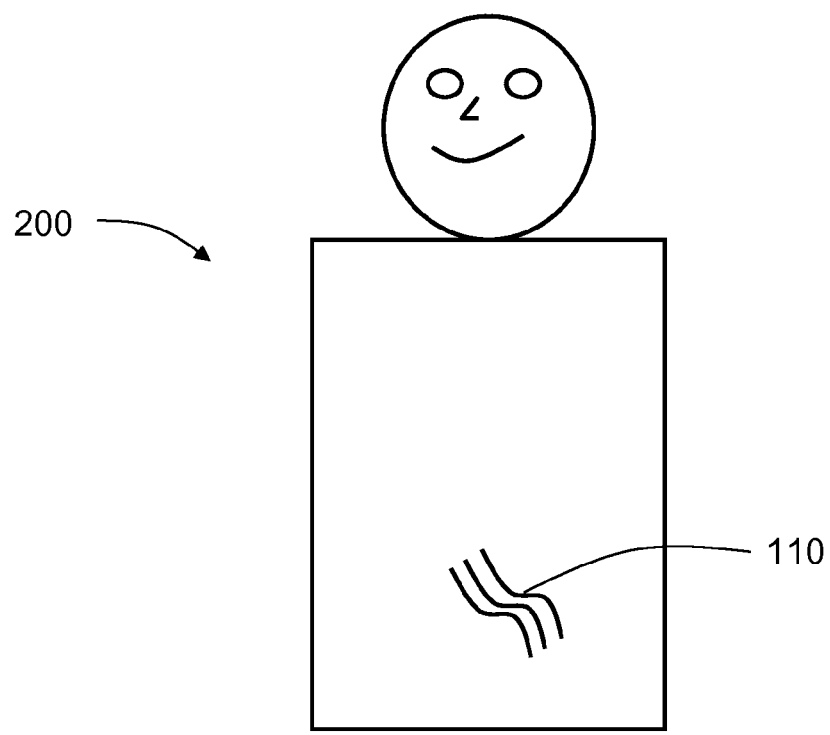
FIG. 11 is a schematic drawing of a patient having a generic region of pain.

Referring to FIG. 11, a patient 100 having a generic region of pain 110 is shown. The region of pain may be any region of pain, such as due to a surgical scar, nerve damage, carpal tunnel or a surgical procedure used to treat carpal tunnel, a scar associated with a herniorrhaphy, thoracotomy, back surgery, hysterectomy, caesarean incision, or the like. While region of pain 110 is depicted as being on the torso of patient 100, it will be understood that the pain may be located at any location of patient 100.

Figure 12:
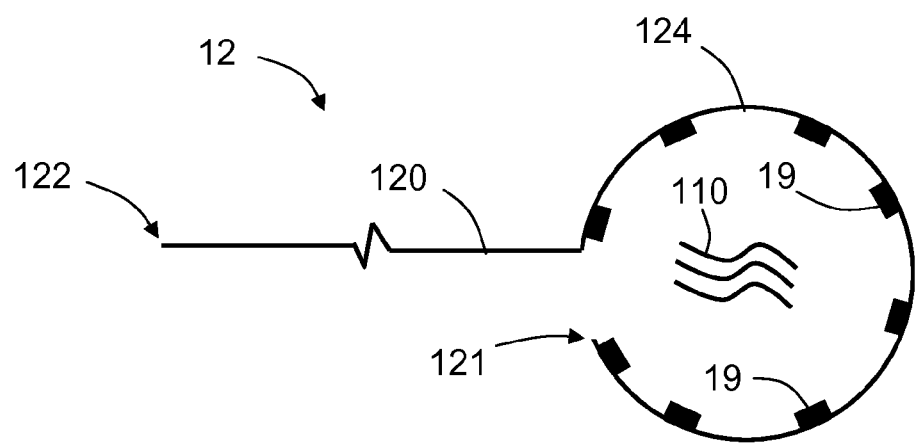
FIG. 12 is a schematic diagram of a implantable medical lead implanted in a patient and bracketing a region of pain.

Referring now to FIG. 12, a lead, or distal portion thereof, 12 is implanted subcutaneously at least partially encircling or bracketing the region of pain 110. The lead 12 may be implanted as described above or using any introducer described or contemplated herein. The lead 12 has a lead body 120 with a proximal end 122 and a distal end 121. Positioned on lead body 120, closer to distal end 121 than proximal end 122, is at least one electrode 19, eight in the illustrated embodiment. Each of electrodes 19 is electrically connected to a contact (not illustrated) at proximal end 12. In some embodiments, each electrode 19 is connected to an individual contact whereas in other embodiments, multiple electrodes 19 (e.g., a pair of any electrodes 19, a pair of adjacent electrodes 19, a pair of opposite electrodes 19, four alternating electrodes 19, etc.) may be connected to a contact.

Lead 14 is implanted to form an arcuate body portion 124, in this embodiment, having all electrodes 19 thereon. Arcuate body portion 124 is positioned such that electrodes 19 at least partially encircle or bracket at least a portion of region of pain 110. In this configuration, at least one electrode 19 is on one side of region of pain 110 and at least one electrode 19 is on a generally opposing side of region of pain 110. By positioning electrodes 19 in such a manner, an electrical signal can be applied to a large area around region of pain 110 through one or more of the plurality of electrodes 19. It is believed that sufficient parasthesia can be produced for pain relief with such a configuration of electrodes, and that such a configuration of electrodes can effectively capture peripheral nerves associated with the pain.

Accordingly, the introducers described herein may be useful for implanting leads for treatment of peripheral pain. However, it will be understood that the introducers described herein may be used to implant leads for any purpose where implanted leads having an arcuate implanted shape is desired.

Figure 13:
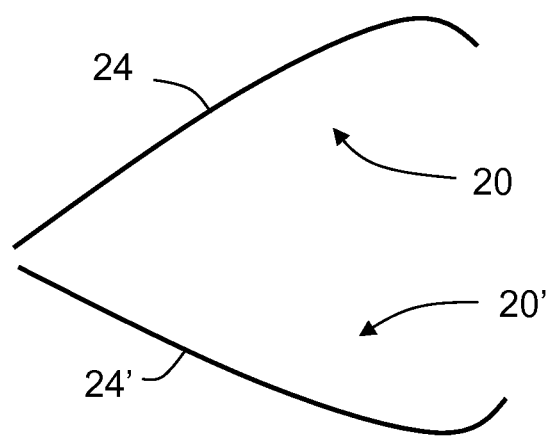
FIGS. 13-14 are schematic top views of arcuate introducers or portions thereof.

Referring now to FIG. 13, arcuate components 24, 24' of introducers 20, 20' having arcuate components 24 with shapes other than semi-circular or helical are shown. The introducers 20, 20' depicted in FIG. 13 may be employed together to implant a lead or leads in a wishbone-shaped manner to bracket a region of interest, such as a region of pain. Of course, arcuatre components of introducers may be of any suitable and desired shape.

Figure 14:
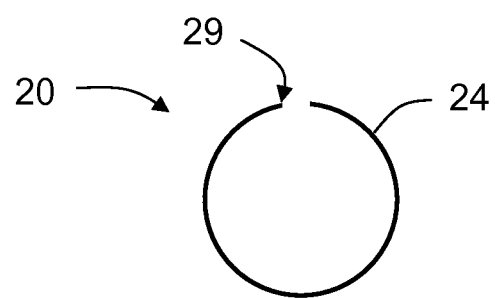

Referring now to FIG. 14, an introducer 20 consisting entirely of an arcuate component 24 is shown. Accordingly, in various embodiments, an introducer as described herein may omit the shaft or the radial component and still be effectively used as an introducer. The body of the arcuate component 24, regardless of whether a shaft is present, may be grasped and fed or pushed as the distal end 29 of the arcuate component 24 is advanced through the patient.

The introducers described herein may be formed from any suitable material or combination of materials. In various embodiment, the introducers or components thereof are formed from metal, alloy, or hard plastic material. Suitable metals or alloys include stainless steel and titanium. The various components may be formed together as a single piece (e.g., molded, extruded, etc.) or may be formed separately and joined (e.g., welding, adhesive, etc.).

In embodiments where the introducer includes a lumen, the lumen is preferably of sufficient diametric dimension to allow free movement of a lead therethrough. In embodiments wherein the introducer is used to pull the lead through tissue of a patient, regardless of whether introducer has a lumen, the outer diametric dimension of the arcuate portion, or a portion thereof, is preferably greater than the outer diametric dimension of the lead so that the introducer creates a path of sufficient size to allow the lead to be readily pulled through the tissue.

Generally, any lead can be used with arcuate introducer described herein. Typically leads are less than about 5 mm in diameter, and may often be between about 1.5-2 mm in diameter. The active surface areas of electrodes may be any suitable size, such as about 1 mm$^2$ to about 100 mm$^2$ (1 cm$^2$), e.g., about 10 mm$^2$ to about 50 mm$^2$ Inter-electrode distances may be about 3 mm, but other inter-electrode distances may be used, such as about 0.5 mm, about 1 mm, about 2 mm, about 4 mm, about 5 mm, about 6 mm, about 7 mm, about 8 mm, about 9 mm, and about 10 mm.

Polyurethane is a preferred material for forming lead body, although other materials such as silicone may be used. Any anchors may be formed of polymer (e.g., polyurethane or silicone) or metal (e.g., platinum, stainless steel, titanium). Electrical conductors extending between proximal end and distal end for supplying electrical current to electrodes are preferably formed of coiled, braided or stranded wires comprising an electrical conductive material, e.g., an MP35N platinum-iridium alloy. Electrodes are preferably formed of platinum, although other metals and metal alloys, such as gold or stainless steel, can be used. In some embodiments, non-metallic yet electrically conductive materials may be used as the electrodes and/or electrical conductors.

It will be understood that electrical signal parameters may be varied as desired for treating pain. Typically, the frequency, amplitude or pulse width of an electrical signal may be varied. An electrical signal having any suitable frequency for treating pain may be used to treat pain as described herein. For example, an electrical signal may have a frequency of about 0.5 Hz to 500 Hz (e.g., about 5 Hz to 250 Hz or about 10 Hz to 50 Hz). For example, the amplitude may be about 0.1 volts to 50 volts (e.g., about 0.5 volts to 20 volts or about 1 volt to 10 volts); for devices that the amps rather than voltage, one skilled in electronics understands the conversion from volts to amps for stimulation devices. An electrical signal may have any suitable pulse width. For example, the signal may have a pulse width of 10 microseconds to 5000 microseconds (e.g., about 100 microseconds to 1000 microseconds or about 180 microseconds to 450 microseconds). For some patients 100 with some devices 10, the determination of the optimal location and parameters for stimulation occurs within days, for others, within hours or minutes.

Thus, embodiments of ARCUATE INTRODUCER are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A system comprising:
   a medical lead; and
   an introducer for introducing the medical lead into a patient, the introducer comprising:
   a shaft;
   a lumen configured to receive the medical lead;
   a radial component; and
   an arcuate component having a proximal end and a distal end, the arcuate component connected to the radial component and the radial component connected to the shaft, wherein the distal end defines a distal opening in communication with the lumen,
   wherein the arcuate component extends along a closed path at least 90degrees and less than 360 degrees,
   and further wherein the introducer is configured such that rotating the shaft results in rotation of the arcuate component to create an arcuate path through subcutaneous tissue, and wherein projecting the introducer onto a plane with a longitudinal axis of the shaft normal to the plane produces an arcuate shape defined by the arcuate component.

2. A system according to claim 1, wherein the arcuate component extends at least 180 degrees along the closed path.

3. A system according to claim 1, wherein the arcuate component has a constant radius from the shaft.

4. A system according to claim 1, wherein the arcuate component and radial component are planar.

5. A system according to claim 1, wherein the shaft is perpendicular to the arcuate component.

6. A system according to claim 1, further comprising a depth control element operably couplable or connected to the shaft.

7. A system according to claim 6, wherein the depth control element is a depth consistency plate operably couplable or connected to the shaft.

8. A system according to claim 1, wherein the lumen extends through the entire arcuate component, the entire radial component, and at least a portion of the shaft to an inlet on the shaft.

9. A system of claim 1, wherein the distal end of the arcuate component comprises a sharp end.

10. A system comprising:
a medical lead; and
an introducer for introducing the medical lead into a patient, the introducer comprising:
a shaft;
a radial component;
an arcuate component having a proximal end and a distal end, the arcuate component connected to the radial component and the radial component connected to the shaft, wherein the distal end defines a distal opening; and
a lumen present through the entire arcuate component, the entire radial component and through at least a portion of the shaft to an inlet on the shaft, the lumen configured to receive the medical lead, wherein the distal opening is in communication with the lumen, wherein the arcuate component extends along a closed path at least 90 degrees and less than 360 degrees, and further wherein the introducer is configured such that rotating the shaft results in rotation of the arcuate component to create an arcuate path through subcutaneous tissue, and wherein projecting the introducer onto a plane with a longitudinal axis of the shaft normal to the plane produces an arcuate shape defined by the arcuate component.

11. A system according to claim 10, wherein the arcuate component extends at least 180 degrees along a closed path.

12. A system according to claim 10, wherein the arcuate component extends at least 270 degrees along a closed path.

13. A system according to claim 10, wherein the arcuate component has a constant radius from the shaft.

14. A system according to claim 10, wherein the arcuate component and radial component are planar.

15. A system according to claim 10, wherein the shaft is perpendicular to the arcuate component.

16. A system of claim 10, wherein the distal end of the arcuate component comprises a sharp end.

17. A method of implanting a lead to at least partially encircle a site, the method comprising:
implanting a lead in proximity to the site by passing the lead through the lumen of a system according to claim 10.

18. A method according to claim 17, wherein implanting comprises rotating the arcuate component around an axis of the introducer.

19. A method according to claim 18, wherein the axis of the introducer is a shaft of the introducer.

20. A method of implanting a lead to at least partially encircle a site, the method comprising:
coupling a distal end portion of a lead to the distal end of the arcuate component of the system of claim 1; and
withdrawing the arcuate component of the introducer from the patient along a curved path such that the lead at least partially encircles the site.

21. A method of implanting a lead to at least partially encircle a site, the method comprising:
coupling a distal end portion of a lead to the distal end of the arcuate component of the system of claim 10; and
withdrawing the arcuate component of the introducer from the patient along a curved path such that the lead at least partially encircles the site.

22. The method of claim 21, wherein the lead is left implanted along the path created by the arcuate component after the arcuate component is withdrawn.

23. The method of claim 20, wherein the lead is left implanted along the path created by the arcuate component after the arcuate component is withdrawn.

24. A system comprising:
a medical lead; and
an introducer for introducing the medical lead into a patient, wherein the introducer in a relaxed unstressed state comprises:
a shaft;
a lumen configured to receive the medical lead;
a radial component; and
an arcuate component having a proximal end and a distal end, the arcuate component connected to the radial component and the radial component connected to the shaft, wherein the distal end defines a distal opening in communication with the lumen,
wherein the arcuate component extends along a closed path at least 90 degrees and less than 360 degrees,
wherein projecting the introducer onto a plane with a longitudinal axis of the shaft normal to the plane produces an arcuate shape defined by the arcuate component.

25. A system of claim 24, wherein the lumen is present through the entire arcuate component, the entire radial component and through at least a portion of the shaft to an inlet on the shaft.

26. A system of claim 24, wherein the introducer is configured such that twisting the shaft results in rotation of the arcuate component to create an arcuate path through subcutaneous tissue.

* * * * *